United States Patent [19]

Lippert et al.

[11] Patent Number: 4,617,410

[45] Date of Patent: Oct. 14, 1986

[54] PROCESS FOR THE PRODUCTION OF PURE CIS-PLATINUM-(II)-IDIAMMINE DICHLORIDE

[75] Inventors: Bernhard Lippert, Garching; Gabriele Raudaschl, Bayerisch Gmain, both of Fed. Rep. of Germany

[73] Assignee: Degussa Aktiengesellschaft, Frankfurt am Main, Fed. Rep. of Germany

[21] Appl. No.: 579,646

[22] Filed: Feb. 13, 1984

[30] Foreign Application Priority Data

Feb. 16, 1983 [DE]  Fed. Rep. of Germany ....... 3305248

[51] Int. Cl.$^4$ ............................................. C07F 15/00
[52] U.S. Cl. .................................. 556/137; 423/131; 514/492
[58] Field of Search .................... 260/429 R; 423/131; 556/137

[56] References Cited

U.S. PATENT DOCUMENTS 4,273,755  6/1981  Rhoda .
4,302,446  11/1981  Kaplan et al. ................. 260/429 R
4,322,391  3/1982  Kaplan .
4,335,087  6/1982  Rhoda .

FOREIGN PATENT DOCUMENTS 0030782  6/1981  European Pat. Off. .
2906700  12/1979  Fed. Rep. of Germany .
2937056  1/1980  Fed. Rep. of Germany .
3134671  6/1982  Fed. Rep. of Germany .
3133443  3/1983  Fed. Rep. of Germany .
2103591  2/1983  United Kingdom .

OTHER PUBLICATIONS

Kaufman, Inorganic Synthesis, vol. VII, pp. 239–240 (1963).
Chemical Abstracts, 44, 5257(1950).
Dhara, Indian J. Chem., 8, pp. 193–194 (1970).
Basolo et al, J. Chemistry, 10, pp. 262–267, (1963).
Chemical Abstracts, 76, 9984a (1972).
Chemical Abstracts, 85, 68907m (1976).
Chemical Abstracts, 84, 80461y (1976).
Chemical Abstracts, 92, 172876f (1980).
Inorganic Chemistry, 215, pp. 2006-2014 (1982).

*Primary Examiner*—Helen M. S. Sneed
*Attorney, Agent, or Firm*—Cushman, Darby & Cushman

[57] ABSTRACT

Cisplatin is purified via an adduct with dimethylformamide. The purified cisplatin is useful as a medicine.

16 Claims, 3 Drawing Figures

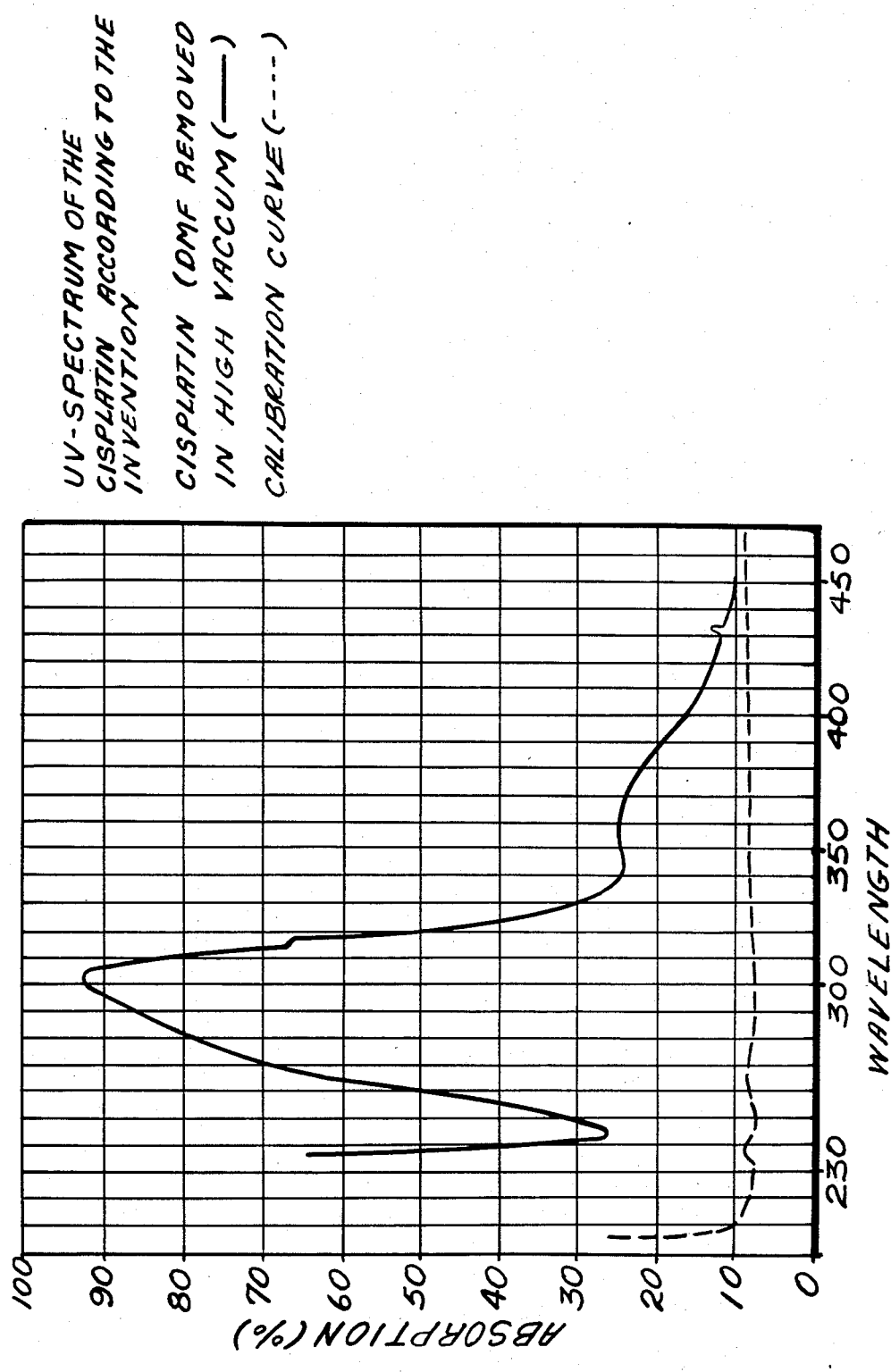

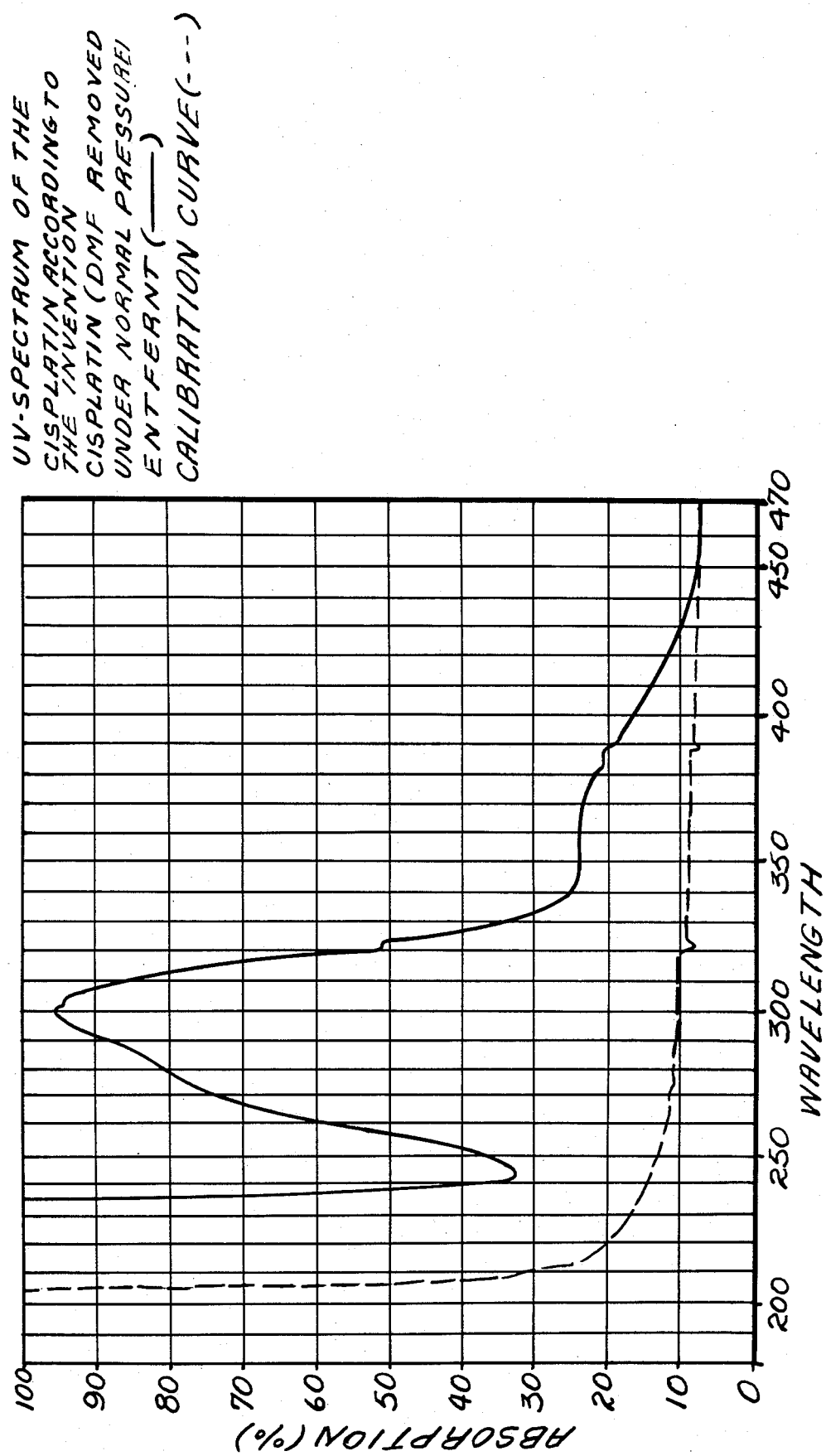

IR-SPECTRUM

PROCESS FOR THE PRODUCTION OF PURE CIS-PLATINUM-(II)-IDIAMMINE DICHLORIDE

BACKGROUND OF THE INVENTION

Cis-platinum-(II)-diammine dichloride which is known under the USAN designation (United States Adopted Name) as cisplatin is used to a great extent as an anti-tumor acting material. However, the cisplatin obtained according to known methods of manufacture is always highly impure and it is suitable for medicinal use only after cumbersome and wasteful purification.

Until now the best known methods of purification consist of a recrystallization of cisplatin from dimethylacetamide in the presence of 0.1N HCl (J. D. Hoeschele, T. A. Butler, J. A. Roberts, C. E. Guyer, Radiochim. Acta, Volume 31, page 27 (1982). This recrystallization, however, results in considerable losses of cisplatin (15-20%). Besides, the cisplatin obtained according to this procedure does not fulfill the purity requirements placed on a medicine.

European patent application No. 30782 discloses purifying cisplatin by recrystallizing from dimethylformamide in the presence of 0.1N HCl at room temperature, e.g. Step 7, page 9. However, there is not obtained an adduct of cisplatin with the dimethylformamide as is obtained in the process of the invention. Besides the yield of cisplatin after the 3rd recrystallization is lower than in the process of the present invention described below.

SUMMARY OF THE INVENTION

The invention is directed to the preparation of purified cisplatin which can be used directly as a medicine.

The purified cisplatin of the invention is particularly useful as an anti-cancer or anti-tumor agent.

According to the invention pure cis-platinum-(II)-diammine dichloride is prepared by reacting cis-platinum-(II)diammine dichloride, e.g. in impure form, with N,N-dimethylformamide to form an adduct and then removing the N,N-dimethylformamide from the adduct. The adduct can be formed by dissolving cis-platinum-(II)-diammine dichloride in N,N-dimethylformamide at a temperature between 12° and 30° C. and subsequently allowing the solution to stand at a temperature between 0° and 5° C.

The N,N-dimethylformamide can be removed in a vacuum. The purified cisplatin obtained can be used for example, with customary pharmacological or pharmaceutically acceptable carriers and/or diluents or adjuvants in medicines.

The process of the invention in a simple manner provides an extraordinarily pure cisplatin.

BRIEF DESCRIPTION OF THE DRAWINGS

FIG. 1a shows the absorption spectrum of cisplatin made according to the invention with the dimethylformamide removed in high vacuum;

FIG. 1b is similar to FIG. 1a but the dimethylformamide is removed at normal pressure.

DETAILED DESCRIPTION

Figure 2:
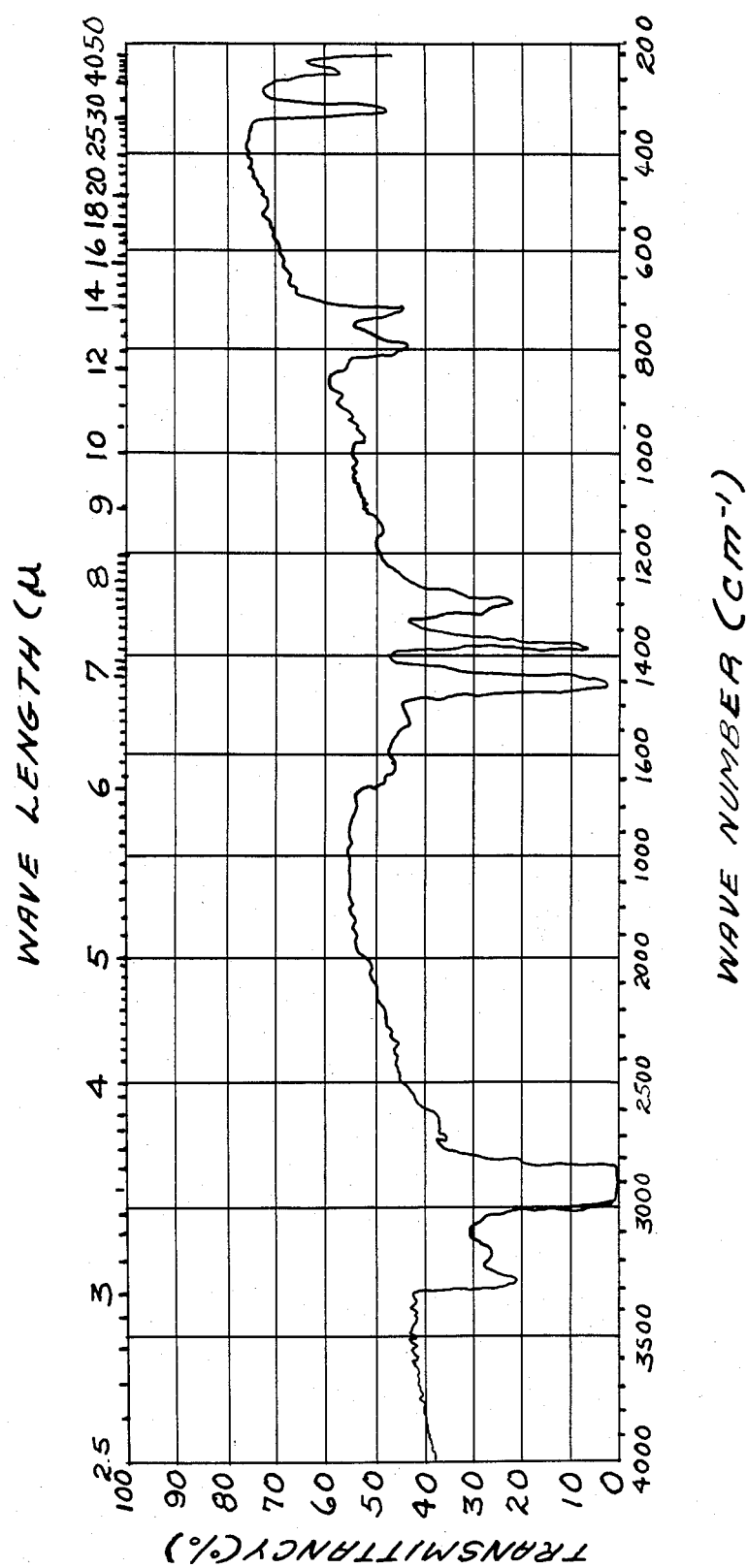
FIG. 2 shows the IR spectrum of the cisplatin (in Nujol) made according to the invention.

The cisplatin obtained according to the process for example, has in its UV spectrum a maximum at 301 nm as well as at 360 nm and a minimum at 246 nm. The extinction coefficient $\epsilon$ at 301 nm is $=132 M^{-1}cm^{-1}$, at 360 nm$=24.8$ and at 246 nm$=27.1$. The UV absorption spectrum was determined with a Cary 17D spectrophotometer using 1 cm cells. The UV-spectrum is pictured in FIG. 1a and FIG. 1b. In each case 50 mg of the cisplatin of the invention was dissolved in 50 ml of 0.1N HCl. With the product according to FIG. 1a the dimethylformamide was removed under high vacuum (1 $\mu$bar) at 20° C. (duration 20 hours). With the product according to FIG. 1b the dimethylformamide was removed simply by allowing the product to stand in the air at 20° C. or 40° C. (in each case 65 hours).

For example, for the cisplatin of the invention the absorption ratio of the absorption of the maximum at 301 nm to the absorption of the minimum at 246 nm is 4.9 (4.86); that of the maximum of 301 nm to the maximum of 360 nm is 5.3 (5.31). The removal of the dimethylformamide hereby is carried out under 1 $\mu$bar at 20° C. during 20 hours.

The IR spectrum of the cisplatin of the invention (measured in Nujol) is shown in FIG. 2.

As starting material for the purification of the invention there can be used cisplatin obtained in customary manner, i.e. a more impure cisplatin than that obtained by the process of the invention. Thus there can be used cisplatin made for example, by the following methods:

Methods of G. B. Kauffman, D. O. Cowan, Inorg. Synth., Volume 7, page 239 (1963); S. C. Dhara, Indian J. Chem., Volume 8, page 193 (1970); V. V. Lebedinskii, G. A. Golovnya, Chem. Abstr., Volume 44, page 5257 (1950). The entire disclosures of this literature is hereby incorporated by reference and relied upon.

The conversion of the impure cisplatin into the adduct with N,N-dimethylformamide is carried out by dissolving cisplatin in N,N-dimethylformamide at a temperature between 12° and 30° C., preferably 15° to 25° C., especially 18° to 22° C.

For example, there are dissolved 2 grams of cisplatin in 85 to 120 ml, preferably 85 to 90 ml of N,N-dimethylformamide. The dissolving is suitably carried out with stirring. For example, the cisplatin crystals can be previously pulverized to a powder, however, there can also be used noncomminuted crystals. The thus obtained solution is filtered (filter size G 4) and the filtrate kept under sealed conditions for a long time (10 to 120, preferably 10 to 40 hours) at $-10°$ to $+5°$, preferably 0° to 3°. The adduct separates out in the form of transparent, lemon yellow crystals. The crystals are filtered off at atmospheric pressure or with suction and washed with a little N,N-dimethylformamide (3 to 10 ml, preferably 5 ml based on 2 grams of cisplatin).

The dimethylformamide is removed from the thus obtained adduct, preferably by evaporation. For example, the adduct is kept for a long time (for example 10 to 70 hours, especially 10 to 30 hours) at a temperature between 15° to 40° C., preferably 18° to 25° C., especially 20° to 22° C. under vacuum (130 mbar to 1 nbar, preferably 20 mbar to 1 $\mu$bar). Especially there is used a high vacuum (for example 1 $\mu$bar to 1 nbar). To completely remove the dimethylformamide there must be used a high vacuum, for example for 10 to 30 hours at room temperature (20° C.).

If there is employed a vacuum lower than a high vacuum (for example under medium vacuum of 133 to 1.33 mbar), there is required, in a given case, for removal of the dimethylformamide more than 30 hours. The same is true if the removal of the dimethylformamide is carried out under normal pressure (1013 mbar)

which likewise is possible. The total removal of the dimethylformamide thus is also possible between for example, normal pressure and 130 mbar. In the simple removal of the dimethylformamide by allowing the adduct to stand in the air under normal pressure, it is suitable for this purpose to take care that the moisture content of the air is not too high; for example, the air should have a relative humidity between 40 and 50%, or even below 40%. In case the dimethylformamide is removed under normal pressure at 20° C. or also at 40° C., there is obtained for example, a cisplatin in which the UV spectrum the absorption ratio of the absorption 301 (or 299) nm/246 nm=4.63 and the absorption ratio of the absorption 301 (or 299) nm/355 nm=5.75. (The second, very flat maximum is now displaced somewhat and is at 355 nm, see FIG. 1b.)

The cisplatin obtained according to the invention is homogenous according to paper chromatography, that is it consists of a single homogeneous spot in the paper chromatogram (independent of whether the removal of the dimethylformamide is carried out under a vacuum or normal pressure).

Test consitions: Paper 2043b of the company Schleicher and Schull, West Germany; the cisplatin is dissolved in a little dimethylformamide; running agent acetone/$H_2O$ (9:1); temperature 20° C.; development via iodine vapor; $R_F$ about 0.4 (see also F. Basolo et al, J. Chromatogr., Volume 10 (1963), page 262.)

To establish whether N,N-dimethylformamide is still present in the cisplatin, samples can be withdrawn and can be tested for example, based on the IR-spectrum (Nujol) for the presence of amide. In case dimethylformamide is still present the standing under normal pressure or the vacuum treatment is continued, namely until there are no longer detectable traces of N,N-dimethylformamide in the IR-spectrum. When there is shown from the UV spectrum at this point in time a ratio $A_{301\ nm}:A_{246\ nm} \geq 4.7$ the treatment is ended (A=absorption). A further indication of the absence of dimethylformamide is shown from the high pressure-liquid chromatogram (UV 220 nm) of a suspension of the product in a 0.1M aqueous solution of NaCl. If there is suspended a cisplatin product which contains N,N-dimethylformamide in as much as possible of a 0.1M NaCl solution, then there is dissolved in the water all of the dimethylformamide present, while the cisplatin remains partially undissolved. The dimethylformamide peak can then be determined quantitatively. The high pressure-liquid chromatogram for example, can be plotted with a customary apparatus for this purpose (for example Philips Pye Unicam; column Li Chrosorb RP 18; Eluent: distilled water; rate of flow 1.2 ml/minute; pressure 220 bar; Detector: UV 220 nm, Recorder: Sensitivity 0.64, velocity 3 cm/minute; samples 15-20 mg cisplatin×dimethylformamide (x=1 to 0) suspended in 1 ml of 0.1M sodium salt solution in water).

The identification of the dimethylformamide peaks is carried out by comparison with pure dimethylformamide in 0.1M sodium chloride solution.

The process can comprise, consist essentially of, or consist of the stated steps with the recited materials.

EXAMPLE 1

2 grams of cisplatin which was produced according to S. C. Dhara, Indian J. Chem., Volume 8, page 193 (1970) were dissolved in 90 ml of N,N-dimethylformamide at room temperature (for example 20° C.) and the solution filtered. The yellow filtrate was kept in a closed flask for 15 hours at 3° C., whereby there separated out light, lemon yellow, transparent crystals. After filtering the crystals were washed with a slight amount of dimethylformamide (5 ml) and then dried briefly on a filter paper in the air. There were obtained 1.5 grams (60% based on the platinum content) of the adduct of cisplatin with N,N-dimethylformamide $Pt(NH_3)_2Cl_2 \cdot C_3H_7NO$. Upon standing in the air the crystals gradually lost the transparency and there resulted the yellow cisplatin (without dimethylformamide). A quantitative removal of the dimethylformamide is produced at 20° C. under high vacuum (for example 1 µbar) during 20 hours (the high vacuum was produced by a mercury diffusion pump).

The entire disclosure of German priority application No. P3305248.4 is hereby incorporated by reference.

What is claimed is:

1. A process for the production of pure cis-platinum-(II)-diammine dichloride comprising reacting impure cis-platinum-(II)-diammine dihydrochloride with N,N-dimethylformamide to form an adduct of the cis-platinum(II) and the N,N-dimethylformamide of the formula $Pt(NH_3)_2Cl_2 \cdot C_3H_7NO$, precipitating the adduct and subsequently removing the N,N-dimethylformamide to recover purified cis-platinum-(II)-diammine dichloride.

2. A process according to claim 1 wherein the adduct is prepared by dissolving the cis-platinum-(II)-diammine dihydrochloride in the N,N-dimethylformamide at a temperature between 12° and 30° C. and subsequently the solution is allowed to stand at a temperature of −10° to +5° C. until the adduct separates out.

3. A process according to claim 2 wherein the solution is allowed to stand at 0° to 5° C.

4. A process according to claim 1 wherein the N,N-dimethylformamide is removed in a vacuum.

5. A process according to claim 4 wherein the N,N-dimethylformamide is removed at 130 mbar to 1 nbar.

6. A process according to claim 5 wherein the pressure is 1 µbar to 1 nbar.

7. Purified cis-platinum-(II)-diammine dichloride prepared by the process of claim 1.

8. Purified cis-platinum-(II)-diammine dichloride prepared according to claim 7 having the IR-spectrum of FIG. 2.

9. Purified cis-platinum-(II)-diammine dichloride prepared according to claim 7 having the UV-absorption spectrum of FIG. 1 of the drawing.

10. Purified cis-platinum-(II)-diammine dichloride according to claim 7 having the UV absorption spectrum of FIG. 1b of the drawing.

11. Cis-platinum-(II)-diammine dichloride having the IR-spectrum of FIG. 2.

12. An adduct of cis-platinum-(II)-diammine dichloride with N,N-dimethylformamide.

13. An adduct according to claim 12 in crystalline form.

14. An adduct according to claim 13 wherein the crystals are transparent and yellow.

15. A process according to claim 1 which comprises precipitating the adduct in crystalline form and then removing the N,N-dimethylformamide to recover purified cis-platinum-(II)diammine dichloride.

16. A process according to claim 15 wherein the materials employed to form the precipitate consist of cis-platinum-(II)diammine dichloride and N,N-dimethylformamide.

* * * * *